United States Patent [19]

Ueda et al.

[11] Patent Number: 4,608,375

[45] Date of Patent: Aug. 26, 1986

[54] QUINAZOLINONE DERIVATIVES, PROCESSES FOR THE PREPARATION THEREOF AND PHARMACEUTICAL COMPOSITION COMPRISING THE SAME

[75] Inventors: Ikuo Ueda, Uenohigashi; Masayuki Kato, Minoo, both of Japan

[73] Assignee: Fujisawa Pharmaceutical Co., Ltd., Osaka, Japan

[21] Appl. No.: 622,881

[22] Filed: Jun. 21, 1984

[30] Foreign Application Priority Data

Jun. 27, 1983 [JP] Japan ................................ 58-116732

[51] Int. Cl.$^4$ ................. A61K 31/445; C07D 239/82; C07D 403/12
[52] U.S. Cl. .................................... 514/218; 540/575; 514/259; 514/826; 544/286; 544/285
[58] Field of Search ................. 514/218, 259; 544/286, 544/285, 287, 297, 292; 260/239 BC

[56] References Cited

U.S. PATENT DOCUMENTS

| | | | |
|---|---|---|---|
| 3,541,151 | 11/1970 | Coombs et al. | 544/286 |
| 3,793,324 | 2/1974 | Denzer | 544/286 |
| 3,970,654 | 7/1976 | Yamamoto et al. | 544/286 |
| 4,199,582 | 4/1980 | Oka et al. | 514/218 |
| 4,200,641 | 4/1980 | Vandenberk et al. | 544/364 |
| 4,247,554 | 1/1981 | Yamamoto et al. | 514/259 |
| 4,335,127 | 6/1982 | Vandenberk et al. | 544/285 |
| 4,430,343 | 2/1984 | Iemura et al. | 514/218 |
| 4,442,084 | 4/1984 | Romer | 514/259 |

*Primary Examiner*—Veronica P. Hoke
*Attorney, Agent, or Firm*—Oblon, Fisher, Spivak, McClelland & Maier

[57] ABSTRACT

The present invention relates to novel quinazolinone derivatives and pharmaceutically acceptable salts thereof. More particularly, it relates to novel quinazolinone derivatives and pharmaceutically acceptable salts thereof which have antiallergic activities, to processes for the preparation thereof, to pharmaceutical composition comprising the same, and to a method of using the same therapeutically in the treatment of allergic symptoms in human being and animals.

6 Claims, No Drawings

QUINAZOLINONE DERIVATIVES, PROCESSES FOR THE PREPARATION THEREOF AND PHARMACEUTICAL COMPOSITION COMPRISING THE SAME

The object quinazolinone derivatives of the present invention are novel and can be represented by the following formula (I):

[Structure (I)]

wherein
$R^1$ is lower alkyl or a group of the formula:

$$-A-N\underset{\phantom{XX}}{\overset{\phantom{XX}}{\diagdown}}N-CH(R^4)_2$$

(wherein A is lower alkylene and $R^4$ is aryl),
$R^2$ is amino, lower alkylamino or a group of the formula:

$$-NH-A-N\underset{(CH_2)_m}{\overset{\phantom{XX}}{\diagdown}}N-CH(R^4)_2$$

(wherein A and $R^4$ are each as defined above and m is an integer of 2 or 3),
a heavy solid line is double bond, and
n is an integer of 0, or
$R^1$ is a group of the formula:

$$-A-N\underset{\phantom{XX}}{\overset{\phantom{XX}}{\diagdown}}N-CH(R^4)_2$$

(wherein A and $R^4$ are each as defined above),
$R^2$ is oxo,
a heavy solid line is single bond,
n is an integer of 1, and
$R^3$ is hydrogen or lower alkyl.

The novel quinazolinone derivatives (I) and pharmaceutically acceptable salts thereof can be prepared by the various methods illustrated as follows:

Process 1

[Structures: (II) + $R^2$—H → (III) or a salt thereof / (I-a) or a salt thereof]

Process 2

[Structures: (IV) or a salt thereof + $R^2$—H → (III) or a salt thereof / (I-a) or a salt thereof]

Process 3

[Structures: (V) + HN$\diagup\diagdown$N—CH($R^4$)$_2$ (VI) or a salt thereof → (I-b) or a salt thereof]

wherein
$R^1$, $R^2$, $R^3$, $R^4$ and A are each as defined above, and X is an acid residue.

Among the starting compounds of the present invention, some of the starting compound (IV) and the starting compound (V) are novel and can be prepared by the following procedures.

Preparation 1

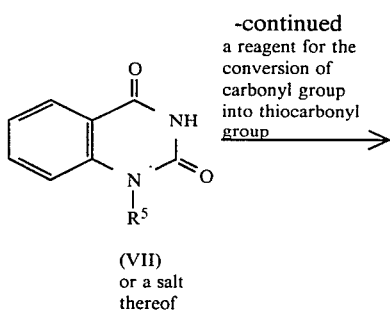

(VII)
or a salt
thereof a reagent for the
conversion of
carbonyl group
into thiocarbonyl
group
⟶

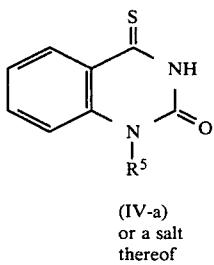

(IV-a)
or a salt
thereof

Preparation 2

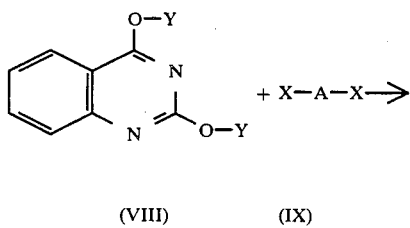

(VIII)     (IX)

(V-a)
or a salt
thereof

Preparation 3

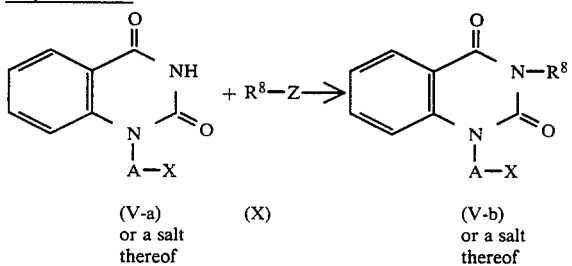

(V-a)      (X)      (V-b)
or a salt           or a salt
thereof             thereof wherein
A and X are each as defined above,
R⁵ is a group of the formula:

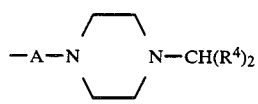

(wherein A and $R^4$ are each as defined above),
$R^8$ is lower alkyl,

Y is trialkylsilyl or a metal, and
Z is an acid residue.

Suitable pharmaceutically acceptable salts of the object compound (I) are conventional non-toxic salts and may include an organic acid salt such as acetate, maleate, oxalate, methanesulfonate, benzenesulfonate, formate, toluenesulfonate or the like, an inorganic acid salt such as hydrochloride, hydrobromide, hydroiodide, sulfate, phosphate or the like, a salt with an amino acid such as arginine, aspartic acid, glutamic acid or the like, and the like.

As to the various definitions as indicated above or below, suitable illustrations and examples are explained in detail as follows.

The term "lower" is intended to mean 1 to 6 carbon atom(s), unless otherwise indicated.

"Lower alkyl" and suitable "lower alkyl" in the term "lower alkylamino" may include the ones having 1 to 6 carbon atom(s) such as methyl, ethyl, propyl, isopropyl, butyl, isobutyl, tert-butyl, pentyl, tert-pentyl, hexyl or the like, preferably the ones having 1 to 4 carbon atom(s).

Suitable "lower alkylene" in the definition "A" may include the ones having 1 to 6 carbon atom(s) such as methylene, ethylene, trimethylene, propylene, tetramethylene, pentamethylene, hexamethylene or the like, preferably the ones having 1 to 4 carbon atom(s).

In the definition "$R^4$", suitable "aryl" may include phenyl, tolyl, xylyl, mesityl, naphtyl and the like.

In the definition "X" and "Z", suitable "acid residue" may include an inorganic acid residue such as azido, halogen (e.g. chlorine, bromine, fluorine or iodine) or the like, an organic acid residue such as acyloxy (e.g. benzenesulfonyloxy, tosyloxy, etc.) or the like.

In the definition "Y", the term "trialkylsilyl" means silyl group which has three alkyl groups as substituents, wherein suitable alkyl may be "lower alkyl" having 1 to 6 carbon atom(s) and suitable examples of said "trialkylsilyl" may include trimethylsilyl, triethylsilyl and the like.

In the definition "Y", suitable "metal" may include alkali metal such as lithium, sodium, potassium or the like.

The processes for preparing the object compound (I) or a salt thereof of the present invention are explained in detail as follows.

Process 1

The object compound (I-a) or a salt thereof can be prepared by reacting a compound (II) with a compound (III) or a salt thereof.

Suitable salts of the compounds (I-a) and (III) can be referred to the ones as exemplified for the object compound (I).

This reaction is usually carried out in a conventional solvent such as chloroform, ether, dioxane, ethanol or any other solvent which does not adversely affect the reaction.

The reaction temperature is not critical and the reaction is preferably carried out at ambient temperature, under warming or under heating.

This reaction is usually carried out in the presence of a base such as alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), trialkylamine (e.g. trimethylamine, triethylamine, etc.) or the like.

Process 2

The object compound (I-a) or a salt thereof can be prepared by reacting a compound (IV) or a salt thereof with a compound (III) or a salt thereof.

This reaction is usually carried out in a conventional solvent such as chloroform, ether, dioxane, ethanol or any other solvent which does not adversely affect the reaction.

The reaction temperature is not critical and the reaction is preferably carried out under warming or under heating.

Process 3

The object compound (I-b) or a salt thereof can be prepared by reacting a compound (V) with a compound (VI) or a salt thereof.

Suitable salts of the compounds (I-b) and (VI) can be referred to the ones as exemplified for the object compound (I).

This reaction is usually carried out in a conventional solvent such as ethanol, acetone, ether, N,N-dimethylformamide or any other solvent which does not adversely affect the reaction.

The reaction temperature is not critical and the reaction is preferably carried out at ambient temperature, under warming or under heating.

This reaction is usually carried out in the presence of a base such as alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), trialkylamine (e.g. trimethylamine, triethylamine, etc.) or the like. Amines (VI) can be used also as a base and liquid base can be used also as a solvent.

The processes for preparing the starting compounds (IV-a), (V-a) and (V-b) of the present invention are explained in detail as follows.

Preparation 1

The compound (IV-a) or a salt thereof can be prepared by reacting a compound (VII) or a salt thereof with a reagent for the conversion of carbonyl group into thiocarbonyl group.

Suitable salts of the compounds (IV-a) and (VII) can be referred to the ones as exemplified for the object compound (I).

Suitable examples of a reagent for the conversion of carbonyl group into thiocarbonyl group may include phosphorus pentasulfide, silicon disulfide, boron sulfide, Lawesson's reagent [2,4-bis(4-methoxyphenyl)-1,3-dithia-2,4-diphosphetane-2,4-disulfide] and the like.

This reaction is usually carried out in a conventional solvent such as carbon disulfide, pyridine, xylene or any other solvent which does not adversely affect the reaction.

The reaction temperature is not critical and this reaction is preferably carried out at ambient temperature, under warming or under heating.

Preparation 2

The compound (V-a) or a salt thereof can be prepared by reacting a compound (VIII) with a compound (IX).

Suitable salts of the compound (V-a) can be referred to the ones as exemplified for the object compound (I).

This reaction can be preferably carried out in an inactive solvent such as chloroform, ether, N,N-dimethylformamide, benzene or the like, and liquid compound (IX) can be also used as a solvent.

The reaction temperature is not critical, and in case that the compound (VIII) to be used has silyl enol ether moiety (i.e. Y is trialkylsilyl), the reaction is preferably carried out under heating and in case that the compound (VIII) to be used has metalated enolate moiety (i.e. Y is a metal) [wherein suitable metal may include alkali metal (e.g. lithium, sodium, potassium, etc.) and the like], the reaction is preferably carried out under cooling or at ambient temperature.

Preparation 3

The compound (V-b) or a salt thereof can be prepared by reacting a compound (V-a) or a salt thereof with a compound (X).

Suitable salts of the compounds (V-b) and (V-a) can be referred to the ones as exemplified for the object compound (I).

This reaction is usually carried out in a solvent such as ethanol, acetone, ether, N,N-dimethylformamide or any other solvent which does not adversely affect the reaction.

The reaction temperature is not critical and the reaction is usually carried out at ambient temperature, under warming or under heating.

This reaction is usually carried out in the presence of a base such as alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), trialkylamine (e.g. trimethylamine, triethylamine, etc.) or the like and liquid base can be used also as a solvent.

In order to illustrate the usefulness of the object compound (I) of the present invention, the pharmacological test data of representative compounds of the present invention are shown as follows.

(A) Test Compounds (1) 1-[3-{4-(Diphenylmethyl)piperazin-1-yl}propyl]-4-methylamino-2-(1H)-quinazoline [hereinafter referred to as Test Compound (1)]

(2) 1-[3-{4-(Diphenylmethyl)piperazin-1-yl}propyl]-2,4(1H, 3H)-quinazolinedione [hereinafter referred to as Test Compound (2)]

(B) Test Compounds (1) Preparation of rabbit antiserum against egg albumin

Equal volumes of a saline solution of egg albumin (200 mg/ml) and of Freund's Complete Adjuvant were mixed and emulsified. Each male New Zealand white strain rabbits, each weighing 2 to 2.5 kg., received an intramuscular injection of 0.5 ml of the emulsion in the left and right thigh regions. One week later, they received an intradermal injection of 0.25 ml of a saline solution of egg albumin (concentration: 20 mg/ml) in the different four sites of the dorsal skin surface three times every other week. Blood samples were collected from the carotid artery one week after the last injection.

(2) Determination of Passive Cutaneous Anaphylaxis (PCA) titer

The level of anaphylactic anti-egg albumin antibodies in pools of sera were determined by passive cutaneous anaphylaxis (PCA) reactions using shaven Hartley strain test guinea-pigs.

Antiserum was serially diluted (twofold) in saline and 0.1 ml of each antiserum dilution were injected intradermally into the dorsal skin surface of the test guinea-pigs. 24 hours after intradermal sensitization, egg albumin-specific PCA reactions were elicited by intravenous injection of 10 mg of egg albumin in 1 ml of 1% Evans blue dye dissolved in saline. Reactions were read and recorded as the highest dilution of serum evoking threshold PCA reactivity (5 mm diameter).

(3) Antagonism to anaphylactic asthma in guinea-pigs

Male Hartley strain guinea-pigs, weighing 307 to 400 g, were used. Animals were sensitized by an intravenous injection of rabbit antiserum against egg albumin (4000 PCA titer) with 0.5 ml/animal. After 24 hours, animals were placed individually in a plastic chamber of 5.3 liter volume. An aerosol of 5% egg albumin solution was sprayed in the chamber for 2 minutes at a rate of 0.16 ml/min with a commercial nebulizer. The test compounds were given to the animals orally 30 minutes before the challenge with the egg albumin solution. Each dose group consisted of 5 animals. The inhibitory effect of the test compounds was determined from the number of animals surviving more than 2 hours after spray of the antigen.

(C) Test Results
Inhibitory effect of anaphylactic asthma in guinea-pig

| Test Compounds | Inhibitory Effect (%) | |
| --- | --- | --- |
| | Dose 10 mg/kg (per oral) | Dose 1 mg/kg (per oral) |
| (1) | 100 | 0 |
| (2) | 100 | 0 |

As being apparent from the above test results, the object compounds (I) of the present invention are useful for the antiallergic medicines.

For therapeutic administration, the object compound (I) and the pharmaceutically acceptable salt thereof of the present invention are used in the form of conventional pharmaceutical preparation which contains said compound as an active ingredient, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade and the like.

If needed, there may be included in the above preparations auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, and the like.

The effective ingredient may usually be administered with a unit dose of 1 mg/kg to 500 mg/kg., 1 to 4 times a day. However, the above dosage may be increased or decreased according to age, weight and conditions of the patient or the administering method.

The following Preparations and Examples are given for the purpose of illustrating the present invention.

Preparation 1

To a mixture of 1-(diphenylmethyl)hexahydro-1H-1,4-diazepine (2.0 g), N-(3-bromopropyl)phthalimide (2.01 g) and anhydrous potassium carbonate (3.1 g) was added acetone (10 ml) and then stirred for 6 hours at 50° C. The reaction mixture was filtered and the filtrate was concentrated in vacuo and then the resultant oily residue was subjected to a column chromatography on silica gel using a mixture of ethyl acetate and chloroform (2:3) for elution to give N-[3-{4-(diphenylmethyl)-hexahydro-1H-1,4-diazepin-1-yl}propyl]phthalimide (2.2 g) as an oil.

IR (CHCl$_3$): 1765, 1705, 1610, 1590 cm$^{-1}$

NMR (CDCl$_3$, δ): 1.70 (4H, m), 2.3–2.7 (10H, m), 3.73 (2H, t, J=8 Hz), 4.53 (1H, s), 7.1–8.0 (14H, m)

Preparation 2

To a mixture of N-[3-{4-diphenylmethyl)hexahydro-1H-1,4-diazepin-1-yl}propyl]phthalimide (2.1 g) and hydrazine hydrate (0.7 ml) was added ethanol (10 ml) and the resultant mixture was refluxed for 2 hours. The reaction mixture was concentrated in vacuo and to the residue was added 1N potassium hydroxide aqueous solution and then the mixture was extracted three times with chloroform. The organic layer was washed with water and with saturated sodium chloride aqueous solution respectively, dried over anhydrous magnesium sulfate and then evaporated in vacuo to give 3-[4-(diphenylmethyl)hexahydro-1H-1,4-diazepin-1-yl]propylamine (1.2 g) as an oil.

The crude product was used in the next step without purification.

IR (CHCl$_3$): 3108, 1665, 1598 cm$^{-1}$

NMR (CDCl$_3$, δ): 1.67 (4H, m), 2.1 (2H, s, This peak was disappeared with D$_2$O), 2.3–2.9 (12H, m), 4.50 (1H, s), 7.0–7.5 (10H, m)

Preparation 3

To a mixture of 1-[3-{4-(diphenylmethyl)piperazin-1-yl}propyl]-2,4-(1H,3H)-quinazolinedione (3.1 g) and phosphorus pentasulfide (6.1 g) was added pyridine (70 ml) and the mixture was stirred for 18 hours at 100° C. The reaction mixture was cooled and then concentrated in vacuo. To the residue was added water and the mixture was stirred and then resultant precipitates were collected by filtration and washed with water. To the precipitates was added chloroform and the mixture was stirred enough and then insoluble materials were filtered off. These insoluble materials were washed twice with chloroform and then whole chloroform layers were combined, washed with water and with saturated sodium chloride aqueous solution respectively, dried over anhydrous sodium sulfate and evaporated in vacuo. The residue was purified by a column chromatography on silica gel (90 g) using 2% methanol in chloroform for elution to give 1-[3-{4-(diphenylmethyl)piperazin-1-yl}propyl]-4-thioxo-3,4-dihydro-2(1H)-quinazolinone (1.2 g) as an amorphous material.

IR (Nujol): 1692, 1605, 1585 cm$^{-1}$

NMR (CDCl$_3$, δ): 1.96 (2H, m), 2.46 (10H, m), 4.20 (3H, m), 7.0–7.8 (13H, m), 8.60 (1H, dd, J=2 and 8 Hz)

Preparation 4

A mixture of 2,4-bis(trimethylsiloxy)-quinazoline (9.14 g) and 1,3-dibromopropane (30 g) was stirred for 2 hours at 130°–140° C. The reaction mixture was cooled at ambient temperature and a mixture of ice-water and saturated sodium bicarbonate aqueous solution was added to the reaction mixture and then the mixture was stirred vigorously to give precipitates. After the mixture was suspended with chloroform, the precipitates were collected by filtration. The precipitates were washed with water and with chloroform respectively and then dried to give 1-(3-bromopropyl)-2,4(1H,3H)-quinazolinedione (2.12 g) as a crystal, which was used in the next step without purification.

m.p. 159°–170° C.

IR (Nujol): 1680, 1602, 1495, 1485 cm$^{-1}$

NMR (DMSO-d$_6$, δ): 2.17 (2H, m), 3.63 (2H, t, J=8 Hz), 4.20 (2H, broad, t, J=8 Hz), 7.2–7.8 (3H, m), 8.06 (1H, dd, J=2 and 8 Hz)

Preparation 5

A mixture of 1-(3-bromopropyl)-2,4(1H,3H)-quinazolinedione (2.83 g), methyl iodide (3 ml), anhydrous potassium carbonate (4.2 g) and N,N-dimethylformamide (25 ml) was stirred for 8 hours at ambient temperature. After the reaction mixture was diluted with cold water, the resultant mixture was extracted twice with chloroform. The chloroform layer was washed with water twice, and with saturated sodium chloride aqueous solution, dried over anhydrous magnesium sulfate and evaporated in vacuo. The resultant oily residue was purified by subjecting to a column chromatography on silica gel (100 g) using chloroform for elution, to give 1-(3-bromopropyl)-3-methyl-2,4(1H,3H)-quinazolinedione (1.85 g) as a crystal.

m.p. 90°–96° C.

IR (Nujol): 1695, 1650, 1602, 1480 cm$^{-1}$

NMR (CDCl$_3$, δ): 2.30 (2H, m), 3.30 (2H, m), 3.47 (3H, s), 4.27 (2H, m), 7.3 (2H, m), 7.70 (1H, m), 8.23 (1H, dd, J=2 and 8 Hz)

EXAMPLE 1

1-Methyl-4-chloro-2(1H)-quinazolinone (1.8 g) and tri(n-propyl)amine (1.5 ml) were dissolved in chloroform (15 ml) and to the resultant solution was added a solution of 3-[4-(diphenylmethyl)hexahydro-1H-1,4-diazepin-1-yl]propylamine (1.2 g) in chloroform (3 ml) and methanol (2 ml). The resultant mixture was stirred for 15 hours at ambient temperature, diluted with water and then extracted with chloroform. The chloroform layer was washed with water and with saturated sodium chloride aqueous solution, dried over magnesium sulfate and then evaporated in vacuo. The resultant oil was purified by subjecting to a column chromatography on silica gel using 4% methanol in chloroform for elution, to give an oily residue (1.3 g). This oily residue was dissolved in methanol and the resultant solution was acidified with conc. hydrochloric acid solution and then concentrated in vacuo, to give a crystal. The resultant crystal was recrystallized three times repeatedly from a mixture of methanol and isopropyl alcohol, to give 1-methyl-4-[3-{4-diphenylmethyl)hexahydro-1H-1,4-diazepin-1-yl}propylamino]-2(1H)-quinazolinone.2.5HCl.0.5H$_2$O (0.9 g).

m.p. 198°–200° C.

IR (Nujol): 3300, 1715, 1635, 1610, 1590, 1530 cm$^{-1}$

NMR (DMSO-d$_6$, δ): 2.30 (4H, m), 3.0–4.1 (12H, m), 3.50 (3H, s), 5.80 (1H, s), 7.1–8.1 (13H, m), 8.60 (1H, d, J=8.0 Hz), 10.15 (1H, broad s)

Analysis for C$_{30}$H$_{35}$N$_5$O.25HCl.0.5H$_2$O Calcd.: C: 61.93, H: 6.67, N: 12.04; Found: C: 61.52, H: 6.66, N: 11.81.

EXAMPLE 2

To a suspension of 1-methyl-4-chloro-2(1H)quinazolinone (4 g), tri(n-propyl)amine (7.2 g) and dioxane (20 ml) was added 3-[4-(diphenylmethyl)piperazin-1-yl]propylamine (3.5 g) and the mixture was stirred for 1.5 hours at ambient temperature. The reaction mixture was concentrated in vacuo and to the residue was added water. After the aqueous layer was made basic with 1N potassium hydroxide aqueous solution, the mixture was extracted twice with chloroform. The chloroform layer was washed with 0.2N potassium hydroxide aqueous solution, with water and with saturated sodium chloride aqueous solution respectively, dried over anhydrous magnesium sulfate and then concentrated in vacuo. After the residue was dissolved in toluene, remaining tri(n-propyl)amine was removed by evaporation in vacuo. This procedure was carried out further twice and then the residual oil was purified by subjecting to a column chromatography on silica gel (70 g) using 2% methanol in chloroform for elution to give a crystal, which was recrystallized from a mixture of ethyl acetate and hexane to give 1-methyl-4-[3-{4-(diphenylmethyl)piperazin-1-yl}propylamino]-2(1H)-quinazolinone (2.4 g).

m.p. 121°–124° C.

IR (Nujol): 3170, 1620, 1600, 1568, 1540 cm$^{-1}$

NMR (DMSO-d$_6$, δ): 1.77 (2H, m), 2.37 (10H, m), 3.46 (3H, s), 3.44 (2H, m), 4.40 (1H, s), 7.0–7.9 (13H, m), 8.13 (1H, d, J=8 Hz), 8.40 (1H, m)

Analysis for C$_{29}$H$_{13}$N$_5$O Calcd. C: 74.47, H: 7.13, N: 14.98; Found: C: 74.23, H: 7.29, N: 14.73.

EXAMPLE 3

A solution of 1-[3-{4-(diphenylmethyl)piperazin-1-yl}propyl]-4-thioxo-3,4-dihydro-2(1H)-quinazolinone (1.2 g) in chloroform (25 ml) and 20% ammonia in methanol (30 ml) was heated in an autoclave for 15 hours at 100° C. The reaction mixture was concentrated in vacuo and the residue was purified by subjecting to a column chromatography on silica gel using 5% methanol in chloroform for elution to give an oily residue. This oily residue was dissolved in methanol and this solution was acidified with conc.hydrochloric acid solution and then concentrated in vacuo to give a crystal of the object compound, which was recrystallized twice from a mixture of water and isoporpyl alcohol to give 1-[3-{4-(diphenylmethyl)piperazin-1-yl}propyl]-4-amino-2(1H)-quinazolinone.2HCl.H$_2$O (0.6 g).

m.p. 190°–196° C.

IR (Nujol): 3600–3100, 1720, 1680, 1615, 1532 cm$^{-1}$

NMR (DMSO-d$_6$, δ): 2.15 (2H, m), 2.6–3.5 (10H, m), 4.26 (2H, m), 4.63 (1H, broad s), 7.1–8.15 (13H, m), 8.63 (1H, d, J=8 Hz), 9.5–11.0 (about 4H, broad s)

Analysis for C$_{28}$H$_{31}$N$_5$O.2HCl.H$_2$O

Calcd.: C: 61.76, H: 6.48, N: 12.86, Cl: 13.02; Found: C: 61.31, H: 6.44, N: 12.77, Cl: 12.77.

EXAMPLE 4

A mixture of 1-[3-{4-(diphenylmethyl)piperazin-1-yl}propyl]-4-thioxo-3,4-dihydro-2(1H)-quinazolinone (1.3 g), 30% methylamine in ethanol (15 ml) and chloroform (15 ml) was heated for 1.5 hours at 60° C. The reaction mixture was concentrated in vacuo and the residue was dissolved in chloroform. The resultant solution was washed with water and with saturated sodium chloride aqueous solution respectively, dried over anhydrous magnesium sulfate and concentrated in vacuo.

The resultant oily residue was purified by subjecting to a column chromatography on silica gel using 3% methanol in chloroform for elution to give a crystal. This crystal was suspended in ethanol and by adding conc. hydrochloric acid solution. The insoluble materials were dissolved. The resultant solution was concentrated in vacuo and then the residue was subjected to crystallization from methanol to give 1-[3-{4-(diphenylmethyl)piperazin-1-yl}propyl]-4-methylamino-2(1H)-quinazolinone.2.4HCl.0.5H$_2$O (1.0 g).

m.p. 238°–240° C.

IR (Nujol): 1735, 1668, 1620 cm$^{-1}$

NMR (DMSO-d$_6$, δ): 2.2 (2H, m), 2.8–3.9 (13H, m), 4.26 (2H, m), 4.6–5.6 (about 4H, m), 7.2–8.2 (13H, m), 8.83 (1H, broad d, J=8 Hz)

Analysis for C$_{29}$H$_{35}$N$_5$O.2.4HCl.0.5H$_2$O Calcd.: C: 61.53, H: 6.83, N: 12.34, Cl: 15.03; Found: C: 61.80, H: 6.34, N: 12.46, Cl: 15.13.

EXAMPLE 5

A mixture of 1-(3-bromopropyl)-2,4(1H,3H)-quinazolinedione (2.12 g), 1-diphenylmethylpiperazine (2.07 g), anhydrous potassium carbonate (3.1 g) and N,N-dimethylformamide (14 ml) was stirred for 2.5 hours at 100° C. After the reaction mixture was cooled to ambient temperature, to the mixture was added water and then stirred to give precipitates. The precipitates were collected by filtration and they were dissolved in hot chloroform containing a little quantity of methanol. The resultant solution was washed with saturated sodium chloride aqueous solution, dried over anhydrous sodium sulfate and concentrated in vacuo to give a crystal, which was washed enough with methanol and dried to give 1-[3-{4-(diphenylmethyl)piperazin-1-yl}propyl]-2,4(1H,3H)-quinazolinedione (1.6 g). This crystal was dissolved in 2N hydrochloric acid solution and then the solution was concentrated in vacuo to give a white crystal, which was washed with methanol, dissolved in water with warming and the solution was evaporated in vacuo. The resultant crystal was washed enough with methanol, to give 1-[3-{4-(diphenylmethyl)piperazin-1-yl}propyl]-2,4(1H,3H)-quinazolinedione.2HCl.0.7H$_2$O (1.6 g).

m.p. 261°–264° C.

IR (Nujol): 3380, 2440, 1712, 1702, 1608 cm$^{-1}$

NMR (DMSO-d$_6$, δ): 2.00 (2H, m), 2.80–4.40 (12H, m), 5.50 (1H, m), 7.0–8.2 (14H, m),

Analysis for C$_{28}$H$_{30}$N$_4$O$_2$.2HCl.0.7H$_2$O Calcd.: C: 62.27, H: 6.23, N: 10.37; Found: C: 62.45, H: 6.06, N: 9.86.

EXAMPLE 6

A mixture of 1-(3-bromopropyl)-3-methyl-2,4(1H,3H)-quinazolinedione (1.68 g), 1-diphenylmethylpiperazine (1.56 g), anhydrous potassium carbonate (2.33 g) and N,N-dimethylformamide (8 ml) was stirred for 3 hours at 60° C. After cooling, water was added to the reaction mixture and then the mixture was extracted twice with chloroform. The chloroform layer was washed with water and with saturated sodium chloride aqueous solution respectively, dried over anhydrous magnesium sulfate and evaporated in vacuo to give an oily residue. This oily residue was dissolved in methanol and then conc.hydrochloric acid solution was dropwise added to the solution to give a crystal, which was collected by filtration, washed with water and dried. This crude crystal was recrystallized from a mixture of methanol and water, to give 1-[3-{4-(diphenylmethyl)piperazin-1-yl}propyl]-3-methyl-2,4(1H,3H)quinazolinedione.2HCl.0.5H$_2$O (2.4 g).

m.p. 250°–253° C.

IR (Nujol): 3580, 3440, 1692, 1640, 1605 cm$^{-1}$

NMR (DMSO-d$_6$, δ): 2.16 (2H, m), 3.33 (3H, s), 3.0–4.6 (10H, m), 4.25 (2H, m), 5.76 (1H, m), 7.4–8.3 (14H, m)

Analysis for C$_{29}$H$_{34}$Cl$_2$N$_4$O$_2$.2HCl.0.5H$_2$O Calcd.: C: 63.26, H: 6.40, N: 10.18; Found: C: 62.60, H: 6.33, N: 10.03.

What we claim is:

1. New quinazolinone derivatives of the formula:

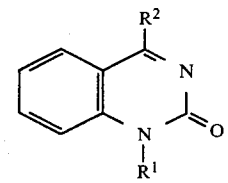

wherein R$^1$ is lower alkyl or a group of the formula:

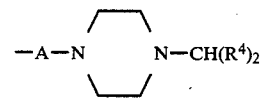

wherein A is lower alkylene and R$^4$ is aryl, R$^2$ is amino, lower alkylamino or a group of the formula:

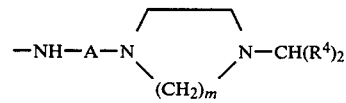

wherein A and R$^4$ are each as defined above and m is an integer of 2 or 3, and pharmaceutically acceptable salts thereof.

2. A compound of claim 1, wherein R$^1$ is methyl or a group of the formula:

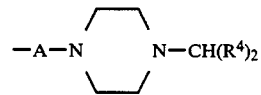

wherein A is propylene and R$^4$ is phenyl, R$^2$ is amino, methylamino or a group of the formula:

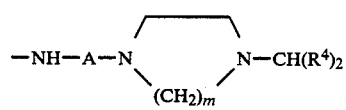

wherein A and R$^4$ are each as defined above and m is an integer of 2 or 3.

3. A compound of claim 2, which is selected from the compounds consisting of:
1-methyl-4-[3-{4-(diphenylmethyl)hexahydro-1H-1,4-diazepin-1-yl}-propylamino]-2(1H)-quinazolinone,
1-methyl-4-[3-{4-(diphenylmethyl)piperazin-1-yl}propylamino]-2(1H)-quinazolinone,
1-[3-{4-(diphenylmethyl)piperazin-1-yl}propyl]-4-amino-2(1H)-quinazolinone, and 1-[3-{4-(diphenylmethyl)ipiperazin-1-yl}propyl]-4-methylamino-2(1H)-quinazolinone.

4. A compound of claim 3, which is 1-[3-{4-(diphenylmethyl)piperazin-1-yl}propyl]-4-methylamino-2(1H)-quinazoline.

5. An antiallergic pharmaceutical composition comprising an effective amount of a compound of claim 1 or a pharmaceutically acceptable salt thereof as an effective ingredient, in association with a pharmaceutically acceptable, substantially nontoxic carrier or excipient.

6. A method for treatment of allergic symptoms which comprises administering an effective amount of a compound of claim 1 to a human being or animal.

* * * * *

UNITED STATES PATENT AND TRADEMARK OFFICE
CERTIFICATE OF CORRECTION

PATENT NO. : 4,608,375
DATED : August 26, 1986
INVENTOR(S) : IKUO UEDA ET AL

It is certified that error appears in the above-identified patent and that said Letters Patent is hereby corrected as shown below:

In column 1, line 16, Formula (I) should be

-- 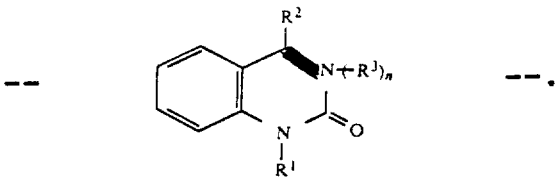 --.

In column 13, line 1, ")ipiperazin" should be --)piperazin--;

line 5, "quinazoline" should be --quinazolinone--.

Signed and Sealed this

Tenth Day of May, 1988

Attest:

DONALD J. QUIGG

Attesting Officer    Commissioner of Patents and Trademarks